(12) United States Patent
Diner et al.

(10) Patent No.: US 8,278,070 B2
(45) Date of Patent: Oct. 2, 2012

(54) ORGANIC SOLVENT PRETREATMENT OF BIOMASS TO ENHANCE ENZYMATIC SACCHARIFICATION

(75) Inventors: Bruce A. Diner, Chadds Ford, PA (US); Janine Fan, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 450 days.

(21) Appl. No.: 12/639,038

(22) Filed: Dec. 16, 2009

(65) Prior Publication Data

US 2010/0159517 A1 Jun. 24, 2010

Related U.S. Application Data

(60) Provisional application No. 61/139,155, filed on Dec. 19, 2008.

(51) Int. Cl.
*C12P 19/00* (2006.01)
*C12P 7/40* (2006.01)
*C12P 7/02* (2006.01)
*C12P 13/04* (2006.01)
*C12P 7/06* (2006.01)
*C12P 7/08* (2006.01)
*C07H 1/08* (2006.01)

(52) U.S. Cl. .......... 435/72; 435/106; 435/136; 435/151; 435/161; 435/163; 536/128

(58) Field of Classification Search .............. 435/72, 435/106, 136, 155, 161, 163; 536/128
See application file for complete search history.

(56) References Cited

U.S. PATENT DOCUMENTS

| | | | |
|---|---|---|---|
| 1,817,525 A | 8/1931 | Richter | |
| 1,891,337 A | 12/1932 | Seaman | |
| 3,033,695 A | 5/1962 | Glab | |
| 3,490,991 A | 1/1970 | Fisher et al. | |
| 3,490,993 A | 1/1970 | Fisher et al. | |
| 4,329,200 A | 5/1982 | Sarkanen | |
| 4,470,851 A | 9/1984 | Paszner et al. | |
| 4,597,830 A | 7/1986 | April et al. | |
| 5,171,592 A | 12/1992 | Holtzapple et al. | |
| 6,555,350 B2 | 4/2003 | Ahring et al. | |
| 2007/0029252 A1 | 2/2007 | Dunson, Jr. et al. | |
| 2007/0031919 A1 | 2/2007 | Dunson, Jr. et al. | |
| 2007/0178569 A1 | 8/2007 | Leschine et al. | |
| 2010/0159518 A1 | 6/2010 | Diner et al. | |
| 2010/0159520 A1 | 6/2010 | Diner et al. | |
| 2010/0178677 A1 | 7/2010 | Dunson, Jr. et al. | |

FOREIGN PATENT DOCUMENTS

| | | |
|---|---|---|
| GB | 925524 A | 5/1963 |
| GB | 1294072 A | 10/1972 |

OTHER PUBLICATIONS

Kleinert, Theodor N., Organosolv pulping with aqueous alcohol, Tappi, Aug. 1974, pp. 99-102, vol. 57, No. 8.
Park, Jung-Keug et al., Ammonia Catalyzed Organosolv Delignification of Poplar, Chemical Engineering Communications, 1988, pp, 187-205, vol. 65.
Lee, Yong-Hyun et al., Evaluation of Organosolv Processes for the Fractionation and Modification of Corn Stover for Bioconversion, Biotechnology and Bioengineering, 1987, pp. 572-581, vol. 29, John Wiley & Sons, Inc.
Peter, Siegfried et al., Degradation of Lignin with Monomethylamine, Chemical Engineering Technology, 1992, pp. 213-217, vol. 15.

*Primary Examiner* — Herbert J Lilling

(57) ABSTRACT

Biomass is pretreated using an organic solvent solution, under alkaline conditions, in the presence of one or more organo-mercaptan and optionally one or more additional nucleophile to fragment and extract lignin. Pretreated biomass is further hydrolyzed with a saccharification enzyme consortium. Fermentable sugars released by saccharification may be utilized for the production of target chemicals by fermentation.

23 Claims, 4 Drawing Sheets

ORGANIC SOLVENT PRETREATMENT OF BIOMASS TO ENHANCE ENZYMATIC SACCHARIFICATION

The application claims the benefit of U.S. Provisional Application No. 61/139,155, filed Dec. 19, 2008, the disclosure of which is hereby incorporated in its entirety.

FIELD OF THE INVENTION

Methods for producing readily saccharifiable carbohydrate-enriched lignocellulosic biomass are provided and disclosed. Specifically, pretreated biomass is prepared through simultaneous fragmentation and selective extraction of lignin with an organic solvent solution in the presence of an organo-mercaptan at elevated temperatures under alkaline conditions. Optionally, one or more nucleophiles may be included as an additional component of the solvent solution. The remaining carbohydrate-enriched solids in the pretreated biomass may then be subjected to enzymatic saccharification to obtain fermentable sugars, which may be subjected to further processing for the production of target products.

BACKGROUND OF THE INVENTION

Cellulosic and lignocellulosic feedstocks and wastes, such as agricultural residues, wood, forestry wastes, sludge from paper manufacture, and municipal and industrial solid wastes, provide a potentially large renewable feedstock for the production of chemicals, plastics, fuels and feeds. Cellulosic and lignocellulosic feedstocks and wastes, composed of cellulose, hemicellulose, pectins and of lignin are generally treated by a variety of chemical, mechanical and enzymatic means to release primarily hexose and pentose sugars, which can then be fermented to useful products.

Pretreatment methods are often used to make the polysaccharides of lignocellulosic biomass more readily accessible to cellulolytic enzymes. One of the major impediments to cellulolytic enzyme digest is the presence of lignin, a barrier that limits the access of the enzymes to their substrates, and a surface to which the enzymes bind non-productively. Because of the significant costs associated with enzymatic saccharification, it is desirable to minimize the enzyme loading by either inactivation of the lignin to enzyme adsorption or its outright extraction. Another challenge is the inaccessibility of the cellulose to enzymatic hydrolysis either because of its protection by hemicellulose and lignin or by its crystallinity. Pretreatment methods that attempt to overcome these challenges include: steam explosion, hot water, dilute acid, ammonia fiber explosion, alkaline hydrolysis (including ammonia recycled percolation), oxidative delignification and organosolv.

Organosolv methods, as previously practiced for the treatment of lignocellulose biomass, for either the production of pulp or for biofuels applications, while generally successful in lignin removal, have suffered from poor sugar recoveries, particularly of xylose. For example, the use of slightly acidic ethanol-water mixtures (e.g., EtOH 42 weight %) at elevated temperature to remove lignin from lignocellulosic biomass (Kleinert, T. N., Tappi, 57: 99-102, 1974) resulted in substantial loss of carbohydrate. Dilute acid hydrolysis at 95° C. followed by organic solvent extraction and enzymatic saccharification (Lee, Y-H., et al., Biotech. Bioeng., 29: 572-581, 1987) resulted in substantial loss of hemicellulose during hydrolysis, additional carbohydrate loss upon organic solvent extraction and poor yield (~50% of total carbohydrate) upon enzymatic saccharification of residue. Use of aqueous organic solvent containing ammonia at elevated temperatures to treat lignocellulosic biomass (Park J.-K. and Phillips, J. A., Chem. Eng. Comm., 65: 187-205, 1988) required the use of a high liquid to solids ratio in pretreatment and resulted in substantial loss of hemicellulose and poor enzymatic saccharification of cellulose. Treatment of biomass with gaseous water and methylamine followed by extraction with organic solvent and then extraction with water, required three steps and resulted in a substantial loss of carbohydrate (Siegfried, P. and Götz, R., Chem. Eng. Technol., 15: 213-217, 1992). Treatment with polyamines or ethylamine in water-aliphatic alcohol mixtures plus catalyst at elevated temperature required high liquid/solids ratio and low concentrations of alcohol led to poor sugar recovery, particularly of xylan (U.S. Pat. No. 4,597,830A). Thioglycolate in aqueous alkaline solution used to treat lignocellulosic biomass at elevated temperature, followed by a hot water wash required use of alkali-metal or alkaline-earth hydroxides. This method requires the costly disposal of inorganic ions, high weight % thioglycolate, and use of large volumes of water (U.S. Pat. No. 3,490,993). Treatment with organic solvent-water mixtures in the presence of sulfide/bisulfide at elevated temperatures required large solvent/solids ratio and resulted in substantial loss of carbohydrate, and elevated sulfur content (U.S. Pat. No. 4,329,200A).

Additional shortcomings of previously applied methods include, separate hexose and pentose streams (e.g., dilute acid), inadequate lignin extraction or lack of separation of extracted lignin from polysaccharide, particularly in those feedstocks with high lignin content (e.g., sugar cane bagasse, softwoods), need to dispose of waste products (e.g., salts formed upon neutralization of acid or base), and poor recoveries of carbohydrate due to breakdown or loss in wash steps. Other problems include the high cost of energy, capital equipment, and pretreatment catalyst recovery, and incompatibility with saccharification enzymes.

One of the major challenges of biomass pretreatment is to maximize the extraction or chemical neutralization (with respect to non-productive binding of cellulolytic enzymes) of the lignin while minimizing the loss of carbohydrate (cellulose plus hemicellulose) via low-cost, efficient processes. The higher the selectivity, the higher the overall yield of monomeric sugars following combined pretreatment and enzymatic saccharification.

There is therefore a need to develop a single step process using substantially lower concentrations of sulfur and recyclable base in the form of ammonia or alkylamines as opposed to the use of alkali metal hydroxides which are not amenable to either recycle or disposal. The current disclosure addresses this need. In this disclosure, organic solvent-mediated fragmentation, in the presence of an organo-mercaptan such as thioglycolate, and selective extraction of lignin at elevated temperatures under alkaline conditions in combination with strong nucleophiles is used. Thioglycolate is added to enhance the fragmentation and extraction of lignin. It does so by the nucleophilic substitution of aryl ethers in the lignin structure. It can also act as a reducing agent, promoting the reduction of quinone methides, driving elimination of β-aryl ethers and protecting sugar residues from oxidative reactions. Surprisingly, the use of thioglycolate in lignocellulosic biomass pretreatment process increases the selectivity of lignin extraction with respect to carbohydrate, producing carbohydrate-enriched biomass that is highly susceptible to enzymatic saccharification. In addition, it is contemplated that thioglycolate, in substitution reactions that displace lignin aryl ethers, introduces carboxyl groups into lignin fragments, thereby increasing their hydrophilicity, making them more soluble in aqueous medium and less likely to adsorb cellulolytic enzyme. Thus, very high yields of fermentable sugars (glucose, as well as xylose) for their bioconversion to value-added chemicals and fuels are achieved.

SUMMARY OF THE INVENTION

The present invention provides methods for producing readily saccharifiable carbohydrate-enriched biomass and for selectively extracting lignin from lignocellulosic biomass while nearly quantitatively retaining carbohydrate. The methods include treating lignocellulosic biomass with an organic solvent solution, such as organosolv, and one of more organo-mercaptans under alkaline conditions at elevated temperatures in a single step. In certain embodiments the solvent solution further comprises additional nucleophilic components such as one or more alkylamines, ammonia, and sulfide reagents. Following pretreatment, the biomass may be further treated with a saccharification enzyme consortium to produce fermentable sugars. These sugars may be subjected to further processing for the production of target products.

Accordingly the invention provides A method for producing carbohydrate-enriched biomass comprising
(a) providing lignocellulosic biomass comprising lignin;
(b) suspending the biomass of (a) in an organic solvent solution comprising water and one or more organo-mercaptan(s) under alkaline conditions whereby a biomass-solvent suspension is formed;
(c) heating the biomass-solvent suspension to a temperature of about 100° C. to about 220° C. for about 5 minutes to about 5 hours whereby lignin is fragmented and is dissolved in the suspension; and
(d) removing the dissolved lignin to produce a carbohydrate-enriched biomass.

In another embodiment the invention provides a method of simultaneous fragmentation and selective extraction of lignin from lignocellulosic biomass to produce a substantially lignin-free biomass, the method comprising the steps of:
(a) providing:
  1) an amount of lignocellulosic biomass;
  2) a multi-component solvent solution comprising from about 40% to about 70% ethanol in water;
  3) one or more organo-mercaptan(s); and
  4) and one or more alkylamine(s) under alkaline conditions;
(b) contacting said biomass with the multi-component solvent solution of (a) to form a solvent-biomass mixture;
(c) placing the solvent-biomass mixture in a sealed pressure vessel whereby the mixture of (b) is heated at a temperature of about 100° C. to about 220° C. for about 5 minutes to about 5 hours whereby lignin is fragmented and dissolved in the solvent;
(d) removing the dissolved lignin of (c) by filtration; and
(e) washing the residual biomass with organic solvent, whereby substantially lignin-free biomass is produced.

In certain embodiments of the above methods, the one or more organo-mercaptan is thioglycolate. In another aspect, one or more alkylamine or an amount of ammonia is present in the solvent solution in addition to the organo-mercaptan. The steps of the methods described herein may be repeated to achieve maximal results. Further, the biomass produced in each method above after step (d) may be washed with water and/or dried and then subjected saccharification for the production of fermentable sugars, which may then be fermented to a target product, such as ethanol.

BRIEF DESCRIPTION OF THE FIGURES

FIG. 1B shows the time course of the production of xylose monomer due to enzymatic saccharification in the presence and absence of 1% Tween 20 (w/v) following pretreatment at 187° C. for 1 h in 70% EtOH in $H_2O$ (v/v) and 14% methylamine (w/w biomass) with or without 2% thioglycolate (w/w biomass).

FIG. 2B shows the UV absorbance spectra of filtrates (diluted 1:5000 with 70% EtOH in $H_2O$) following pretreatment at 187° C. in 70% EtOH in $H_2O$ (v/v) plus 14% methylamine (w/w biomass) and with 14% methylamine (w/w biomass) plus 2% glycolic acid (w/w biomass) or 2% glycine (w/w biomass).

DETAILED DESCRIPTION OF THE INVENTION

Figure 1A:
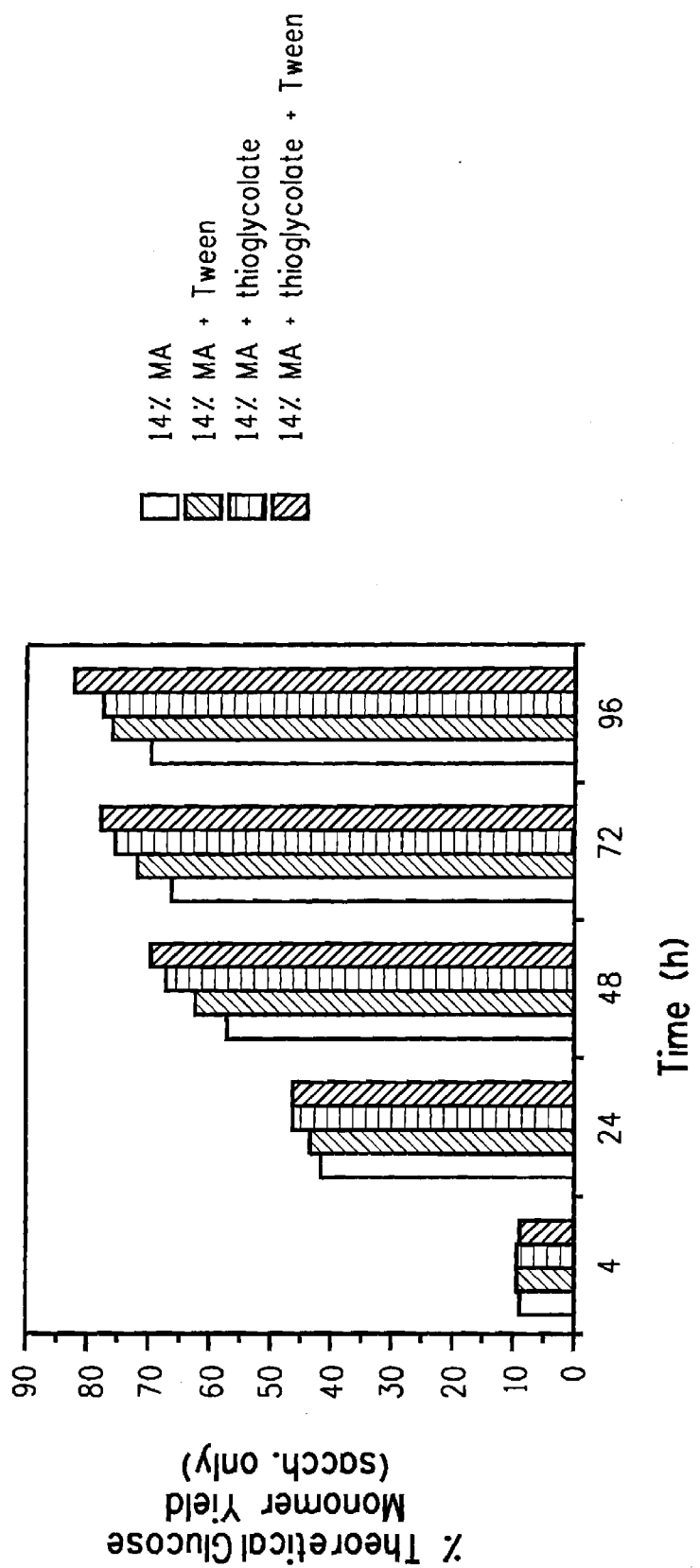
FIGS. 1A and 1B—FIG. 1A shows the time course for the production of glucose monomer due to enzymatic saccharification in the presence and absence of 1% Tween 20 (w/v) following pretreatment at 187° C. for 1 h in 70% EtOH in $H_2O$ (v/v) and 14% methylamine (w/w biomass) with or without 2% thioglycolate (w/w biomass).

Applicants specifically incorporate the entire content of all cited references in this disclosure. Unless stated otherwise, all percentages, parts, ratios, etc., are by weight. Trademarks are shown in upper case. Further, when an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention provides a process for the treatment of biomass in order to produce readily saccharifiable carbohydrate-enriched biomass to enhance the subsequent enzymatic saccharification step such that readily fermentable sugars can be obtained from saccharification. A process involving a pretreatment step wherein lignin is simultaneously fragmented and selectively extracted using alkaline organosolv conditions at elevated temperatures in the presence of one of more organo-mercaptans and added nucleophiles is employed. The treated biomass is then filtered and washed to remove solubilized lignin, acetic acid, acetamides, alkylamides and excess reagent and then digested with a saccharification enzyme consortium to produce readily fermentable sugars. The sugars may then be further processed to one or more target product. The removed lignin may also be further processed and utilized for other purposes (such as burning for energy) to increase efficiency.

Definitions

The following definitions are used in this disclosure:

"Room temperature" and "ambient" when used in reference to temperature refer to any temperature from about 15° C. to about 25° C.

"Fermentable sugars" refers to a sugar content primarily comprising monosaccharides and some disaccharides (that can be used as a carbon source by a microorganism (some polysaccharides may be present)) in a fermentation process to produce a target product. "Readily fermentable sugars" means that additional costly processing is not necessary and/or that a fermentative microorganism can be contacted with the resulting sugars with minimal impediments from inhibitors or other components that may adversely affect fermentation.

"Lignocellulosic" refers to material comprising both lignin and cellulose. Lignocellulosic material may also comprise hemicellulose. In the processes described herein, lignin is dissolved and substantially removed from the lignocellulosic biomass to produce a carbohydrate-enriched biomass.

"Dissolved lignin" as referred to herein means the lignin that is dissolved in an organic acid solvent solution.

"AI lignin" refers to acid-insoluble lignin.

"Autohydrolysis" refers to the hydrolysis of biomass in the presence of solvent (water or organic solvent plus water) plus heat with no further additions, such as without exogenous acid or base or hydrolytic enzyme addition.

"Cellulosic" refers to a composition comprising cellulose.

"Target product" refers to a chemical, fuel, or chemical building block produced by fermentation. Product is used in a broad sense and includes molecules such as proteins, including, for example, peptides, enzymes and antibodies. Also contemplated within the definition of target product are ethanol and butanol.

"Dry weight of biomass" refers to the weight of the biomass having all or essentially all water removed. Dry weight is typically measured according to American Society for Testing and Materials (ASTM) Standard E1756-01 (Standard Test Method for Determination of Total Solids in Biomass) or Technical Association of the Pulp and Paper Industry, Inc. (TAPPI) Standard T-412 om-02 (Moisture in Pulp, Paper and Paperboard).

"Selective extraction" means removal of lignin while substantially retaining carbohydrates.

"Solvent solution" or "an organic solvent solution", as used herein, is an organic solvent mixture in water that includes any organic liquid that dissolves a solid, liquid, or gaseous solute, resulting in a solution. The most suitable solvent solutions for this invention are organic solvents such as ethanol, methanol, n-propanol, isopropanol, n-butanol, 2-butanol, isobutanol, t-butanol, pentanol and hexanol and diols with the same number of carbons. They can also include aprotic solvents. The solvent solutions can include additional components in mixture with the solution, e.g., the solvent solution may include one or more nucleophile.

"Biomass" and "lignocellulosic biomass" as used herein refer to any lignocellulosic material, including cellulosic and hemi-cellulosic material, for example, bioenergy crops, agricultural residues, municipal solid waste, industrial solid waste, yard waste, wood, forestry waste and combinations thereof, and as further described below. Biomass has a carbohydrate content that comprises polysaccharides and oligosaccharides and may also comprise additional components, such as protein and/or lipid.

"Highly conserved" as used herein refers to the carbohydrate content of the lignocellulosic material after the processing steps described herein. In an embodiment of the invention, the highly conserved carbohydrate content provides for sugar yields after saccharification that are substantially similar to theoretical yields with minimal loss of sugar yield from the processes described herein. In an embodiment of the invention, highly conserved with reference to carbohydrate content refers to the conservation of greater than or equal to 85% of the biomass carbohydrate as compared to biomass prior to pretreating as described herein.

"Preprocessing" as used herein refers to processing of lignocellulosic biomass prior to pretreatment. Preprocessing is any treatment of biomass that prepares the biomass for pretreatment, such as mechanically milling and/or drying to the appropriate moisture contact.

"Biomass-solvent suspension" refers to a mixture of biomass and solvent. The biomass-solvent solution may comprise additional components such as alkylamines, thioglycolate, ammonia, sulfides, etc.

"Saccharification" refers to the production of fermentable sugars from primarily polysaccharides by the action of hydrolytic enzymes. Production of fermentable sugars from pretreated biomass occurs by enzymatic saccharification by the action of cellulolytic and hemicellulolytic enzymes.

"Pretreating biomass" or "biomass pretreatment" as used herein refers to subjecting native or preprocessed biomass to chemical or physical action, or any combination thereof, rendering the biomass more susceptible to enzymatic saccharification or other means of hydrolysis prior to saccharification. For example, the methods claimed herein may be referred to as pretreatment processes that contribute to rendering biomass more accessible to hydrolytic enzymes for saccharification.

"Pretreatment filtrate" means the free liquid that is in contact with the biomass following pretreatment and which is separated by filtration.

"Pretreated Biomass" as used herein refers to native or preprocessed biomass that has been subjected to chemical or physical action, or any combination thereof, rendering the biomass more susceptible to enzymatic saccharification or other means of hydrolysis prior to saccharification.

"Air-drying the filtered biomass" can be performed by allowing the biomass to dry through equilibration with the air of the ambient atmosphere.

"Readily saccharifiable biomass" means biomass that is carbohydrate-enriched and made more amenable to hydrolysis by cellulolytic or hemi-cellulolytic enzymes for producing monomeric and oligomeric sugars, i.e., pretreated biomass as described herein.

"Carbohydrate-enriched" as used herein refers to the biomass produced by the process treatments described herein. In one embodiment the readily saccharifiable carbohydrate-enriched biomass produced by the processes described herein has a carbohydrate concentration of greater than or equal to 85% of the dried biomass by weight, while having removed 75% or greater of the starting biomass lignin content based on dry weight.

"Heating the biomass suspension" means subjecting the biomass suspended in a solvent to a temperature greater than ambient or room temperature. Temperatures relevant to the present pretreatments are from about 100 to about 220° C., or from about 140 to about 180° C., or any temperature within or approximately these ranges.

"Filtering free liquid under pressure" means removal of unbound liquid through filtration, with some pressure difference on opposite faces of the filter.

"Alkaline" or "under alkaline conditions" means a pH of greater than 7.0. In the present invention, "under alkaline conditions", also means a pH of the biomass-solvent suspension equal to or greater than the pKas of the nucleophiles present such that these are substantially deprotonated and more highly reactive than in their protonated states. These nucleophiles would include alkylamines, and ammonia, thiols, polysulfides and hydrosulfide (if present).

"Divalent alkane" means a linear, branched or cyclic alkane with two open valences.

"Thiols" or "organo-mercaptans" are compounds that contain a functional group composed of a sulfur atom and a hydrogen atom (—SH). For example, thioglycolic acid (TGA) is the organic compound with the general formula of $HSCH_2CO_2H$. It contains both a thiol (mercaptan) and a carboxylic acid and is a clear liquid that can also act as a reducing agent, becoming oxidized to the corresponding disulfide $[SCH_2CO_2H]_2$. Other examples of thiols in common usage are 2-mercaptoethanol, dithiothreitol, dithioerythritol, cysteine, glutathione, methanethiol, mono-and disubstituted ethane, propane and butane thiols.

"Alkylamine" means an alkane containing an —$NH_2$ group in place of one, two or three H atoms; e.g., ethylamine, monomethylamine, dimethylamine, trimethylamin, isopropylamine, ethylhexylamine, cyclohexylamine, and as further defined below.

"Air-dried sample" means a pretreated sample which has been allowed to air-dry at ambient temperature and pressure to the point where its moisture content is in equilibrium with that of the ambient air, typically ≧85% dry matter.

"Substantially lignin-free biomass" means a pretreated sample in which about ≧75% of the lignin is removed.

"Dry biomass" means biomass with a dry matter content of ≧85%. Methods for drying the biomass include exposure at ambient temperature to vacuum or flowing air at atmospheric pressure and or heating in an oven or a vacuum oven.

"Multi-component solvent" means a solvent containing organic solvent, water, and reagents capable of chemical attack on the lignin.

"Pressure vessel" is a sealed vessel that may be equipped or not with a mechanism for agitation of a biomass/solvent suspension, in which a positive pressure is developed upon heating the lignocellulosic biomass.

"Nucleophile" is a chemical reagent capable of forming a covalent bond with its reaction partner by contributing both of the bonding electrons.

"Hydrolysate" refers to the liquid in contact with the lignocellulose biomass which contains the products of hydrolytic reactions acting upon the biomass (either enzymatic or not), in this case monomeric and oligomeric sugars.

"Organosolv" means a mixture of organic solvent and water which is typically in contact with biomass and in which the lignin or its fragments are soluble.

"Enzyme consortium" or "saccharification enzyme consortium" is a collection of enzymes, usually secreted by a microorganism, which in the present case will typically contain one or more cellulases, xylanases, glycosidases, ligninases and esterases.

"Monomeric sugars" or "simple sugars" consist of a single pentose or hexose unit, e.g., glucose, xylose and arabinose.

"Delignification" is the act of removing lignin from lignocellulosic biomass. In the context of this application, delignification means fragmentation and extraction of lignin from the lignocellulosic biomass using an organic solvent under alkaline conditions at elevated temperatures in the presence of organo-mercaptans and optionally various nucleophiles.

"Simultaneous fragmentation and selective extraction" as used herein refers to a fragmentation reaction performed in organic solvent such that the lignin fragments go into solution as soon as they are released from the bulk biomass.

"Fragmentation" is a process in which lignocellulosic biomass is treated under organosolv conditions breaking the lignin down into smaller subunits.

"Selective extraction" is a process by which fragmented lignin is dissolved by treatment with an organic solvent under alkaline conditions leaving behind the polysaccharide.

Methods for pretreating lignocellulosic biomass to produce readily saccharifiable biomass are provided. These methods provide economic processes for rendering components of the lignocellulosic biomass more accessible or more amenable to enzymatic saccharification. The pretreatment can be chemical or physical, or any combination of the foregoing. In this disclosure the pretreatment is performed in the presence of nucleophiles, specifically in the presence of one or more organo-mercaptan such as thioglycolate under alkaline conditions. Additional nucleophiles may also be present, such as $NH_3$, one or more alkylamines, sulfide reagents, or combinations thereof. The presence of an organic solvent and alkaline conditions assists lignin fragmentation and removal and carbohydrate recovery. In addition, the methods described in the present disclosure minimize the loss of carbohydrate during the pretreatment process and maximize the yield of solubilized (monomeric+oligomeric) sugars in saccharification.

As disclosed above the methods described herein include pretreating lignocellulosic material, with a solvent solution comprising the components described below, to produce a readily saccharifiable carbohydrate-enriched biomass.

Solvents

The methods described herein include use of an organic solvent for pretreating biomass and specifically for fragmentation and extraction of lignin. Solvents useful in the present methods are frequently referred to in the art as Organosolv (e.g., E. Muurinen (2000) Organosolv Pulping, A review and distillation study related to peroxyacid pulping Thesis, University of Oulu, pp. 314; S. Aziz, K. Sarkanen, Tappi J., 72/73: 169-175, 1989; A. K. Varsheny and D. Patel, J. Sci. Ind. Res., 47: 315-319, 1988; A. A. Shatalov and H. Pereira, BioResources 1:45-61, 2006; T. N. Kleinert, Tappi J., 57: 99-102, 1979; Practice of organosolv technology for biofuels, derived from Kleinert, which has advanced to the pilot scale using EtOH in $H_2O$ has been described (WO 20071051269), and X. Pan, N. Gilkes, J. Kadla, K. Pye, S. Saka, D. Gregg, K. Ehara, D. Xie, D. Lam, and J. Saddler, Biotechnol. Bioeng., 94: 851-861, 2006. While still at lab scale, use of acetone/$H_2O$ is described in U.S. Pat. No. 4,470,851. Further details on pretreatment technologies related to use of solvents and other pretreatments can be found in Wyman et al., (Bioresource Tech., 96: 1959, 2005); Wyman et al., (Bioresource Tech., 96: 2026, 2005); Hsu, ("Pretreatment of biomass" In Handbook on Bioethanol: Production and Utilization, Wyman, Taylor and Francis Eds., p. 179-212, 1996); and Mosier et al., (Bioresource Tech., 96: 673, 2005). Solvents are used herein for pretreating biomass to remove lignin. Delignification is typically conducted at temperatures of 165-225° C., at liquid to biomass ratios of 4:1 to 20:1, at liquid compositions of 50% organic solvent (v/v), and at reaction times between 0.5-12 h. A number of mono-and polyhydroxy-alcohols have been tested as solvents. Ethanol, butanol and phenol have been used (Park, J. K., and Phillips, J. A., Chem. Eng. Comm., 65: 187-205, 1988).

The organosolv or organic solvent solution pretreatment in the present methods may comprise a mixture of water and an organic solvent at selected condition parameters that include temperature, time, pressure, solvent-to-water ratio and solids-to-liquid ratio. The solvent can comprise, but is not limited to, alcohols and aprotic solvents (solvents that do not have a hydrogen atom bound to an oxygen as in a hydroxyl group or a nitrogen as in an amine group or a sulfur as in a thiol group, e.g., ketones). The alcohols may include methanol, ethanol, propanol, butanol, pentanol and hexanol and isomers thereof and diols with the same number of carbon atoms, such as 1,2-ethandiol, 1,2-propanediol, 1,3-butanediol, 1,3-pentanediol, and 1,3-hexanediol.

The concentration of the solvent in solution (i.e. water) in the present invention is from about 2 to about 90% (v/v), or from about 10% to about 85% or from about 20% to about 80% or from about 30% to about 80% or more preferably from about 40% to about 70% (v/v). Specifically, for purposes of an embodiment of the methods herein, EtOH in $H_2O$ mixtures from about 0%-80% (v/v) ethanol was examined and solution containing 40-70% (v/v) EtOH were found to be most effective.

Organo-Mercaptans

Organo-mercaptans are used for pretreatment of biomass according to the present methods as components of the solvent solution. Examples of organo-mercaptans that may be used in this invention are those containing the general formula (I) HS—R—(Y)$_n$ wherein "R" represents a divalent radical, more particularly a divalent hydrocarbon radical, "Y" represents a monovalent substituent bonded directly to "R", and "n" represents a numeral ranging from 0 up to the combining power (i.e., a value that will completely satisfy all valances) of the divalent radical represented by "R". Preferably the divalent hydrocarbon radical represented by "R" contains not more than 10 carbon atoms, more particularly from 1 to 8 carbon atoms.

Particularly useful in practicing the present invention are organo-mercaptans represented by the general formula HS—R—(COOZ)$_n$, wherein "R" represents an alkylene (including cycloalkylene) radical containing from 1 through 10, and preferably from 1 through about 8, carbon atoms; Z represents a member of the group consisting of (a) hydrogen (a thio acid), (b) alkyl radicals containing not more than about 10 carbon atoms and preferably a lower alkyl radical (e.g., an alkyl radical containing from 1 through about 6 carbon atoms) (an ester); and (c) a salt-forming cation (a salt); and "n" represents an integer from 1 up to that of the combining power of the alkylene radical represented by "R" The alkylene radical represented by "R" may be straight-chain, branched-chain, or cyclic as in, for example, cyclopentyl, cyclohexyl, and the like. Thus, preferred compounds embraced by this formula may be the thio acid itself or a salt (especially a water-soluble salt) or an ester of such an acid. Of these compounds thioglycolic acid and the water-soluble salts and the lower alkyl esters thereof are the more preferred sub-group.

A single organo-mercaptan or a plurality of different organo-mercaptans may be employed; or, one or more organo-mercaptans may be used in conjunction with one or more inorganic treating agents including, for example, sodium sulfhydrate (sodium hydrosulfide, NaSH), sodium sulfide, sodium polysulfide, $Na_2S_x$, sodium borohydride, $NaBH_4$, and the like.

The proportion of organic thio treating agent, e.g., TGA, with respect to lignocellulosic biomass may be within the range of 0-15 wt % of biomass. The upper limit of the organo-mercaptan component is not critical, but because of its relatively high cost it is economically desirable to use no more of it in the process than is required to affect the desired result.

The substantially pure organic thio compound, or a crude form thereof such as is obtained commercially in its preparation, or mixtures of organic thio compounds may be employed as the reactive agent or component of the treating liquor. Minor amounts (less than 50% by weight) of inorganic thio reactants, e.g., sodium sulfhydrate, sodium sulfide, sodium polysulfide, etc, may be used in the form of an admixture with the organic thio compound.

In accordance with the present methods it has been unexpectedly discovered that organo-mercaptan (e.g., TGA) addition to the solvent solution under alkaline conditions resulted in increased lignin fragmentation and extraction, and accordingly, increased accessibility of the carbohydrate-enriched biomass to enzymatic saccharification. Specifically, in combination with an alkylamine, the presence of thioglycolate yielded a surprising effective amount of fermentable sugars following enzymatic saccharification.

In the present invention, concentrations of organo-mercaptans employed range from about 0.5 to about 15% wt % of dry biomass, e.g., a concentration of thioglycolate from about 0.5 to about 15% wt % of dry biomass could be used. More specifically, concentrations of 1 to 3 wt % of dry biomass are more useful. Even more specifically concentrations of ~2 wt % of dry biomass would be most useful for the present invention.

Additional Components of the Solvent Solution

In one embodiment, in addition to one of more organo-mercaptan, alkylamines are used, under alkaline conditions, for pretreatment of biomass according to the present methods as components of the solvent solution. Alkylamines are strong bases owing to electron donation to the amine nitrogen by the alkyl chain carbons, and consist of primary amines (R—$NH_2$), secondary amines (R—N—R') and tertiary amines where R is an alkyl chain. Specifically R could be selected from a group consisting of a monovalent, divalent or trivalent 1-6 carbon alkane, alkene or alkyne, linear, cyclic or branched. Examples of alkylamines include, mono, di-and tri-methylamine, mono, di-and tri-ethylamine, mono, di-and tri-propylamine, mono, di-and tri-butylamine. Alkylamines include mono-, di-and tri-amines, alcohol amines (HO—R—$NH_2$), diolamines ((HO)$_2$—R—$NH_2$), alcohol diamines (HO—R—(NH$_2$)$_2$), thiolamines (HS—R—$NH_2$), dithioamines ((HS)$_2$—R—$NH_2$), thioldiamines (HS—R—(NH$_2$)$_2$) and alcohol thiolamines ($H_2$N—R(OH)(SH) where R is as defined.

Suitable alkylamines for this invention comprise: methylamine (MA), dimethylamine (DMA), trimethylamine (TMA), ethylamine, propylamine, and butylamine. The more suitable alkylamines for this invention include, but are not limited to MA and DMA. The concentration of the alkylamines according to the present method may be used from about 1% to about 20 wt % of dry biomass. In accordance with the present methods alkylamines, especially MA and DMA, are highly active in a concentration range of from 10% to 14% relative to dry weight of biomass.

According to the present method, the solvent solution comprising one or more organo-mercaptan may optionally comprise additional components. The additional components may include other nucleophiles such as at least one additional (inorganic) base, such as sodium hydroxide, ammonia, sodium carbonate, potassium hydroxide, potassium carbonate, calcium hydroxide and calcium carbonate.

The one or more additional base may be added in an amount that is combined with organo-mercaptan to form an amount of total base that is less than about 20 wt % relative to biomass dry weight. Preferably the total one additional base plus organo-mercaptan is in an amount that is less than about 16%, or about 0%, 2%, 4%, 6%, 8%, 10%, 12%, 14% or 16% relative to dry weight of biomass. The one or more additional base may be used at various concentrations of at least from 0.5% to about 16%. More suitable are the concentrations from 1% to 10%. Most suitable are the concentrations between 2% to 8%.

Furthermore NaOH may be employed as an additional component of the solvent solution in the presence of alkylamines resulting in increasing lignin fragmentation and extraction, and resulting in an increased accessibility of the carbohydrate-enriched biomass to enzymatic saccharification. NaOH may be used specifically in an EtOH in $H_2O$ solvent mixture/solution and use of NaOH may include the addition of a catalyst, such as anthraquinone, to the solvent solution for further lignin fragmentation.

Lignocellulosic Biomass

The lignocellulosic biomass pretreated herein includes, but is not limited to, bioenergy crops, agricultural residues, municipal solid waste, industrial solid waste, sludge from paper manufacture, yard waste, wood and forestry waste. Examples of biomass include, but are not limited to corn cobs, crop residues such as corn husks, corn stover, grasses, wheat, wheat straw, barley, barley straw, hay, rice straw, switchgrass, waste paper, sugar cane bagasse, sugar cane straw, yellow poplar, sorghum, soy, components obtained from milling of grains, trees, branches, roots, leaves, wood chips, sawdust, shrubs and bushes, vegetables, fruits, flowers and animal manure.

In one embodiment, the lignocellulosic biomass includes agricultural residues such as corn stover, wheat straw, barley straw, oat straw, rice straw, canola straw, and soybean stover; grasses such as switchgrass, miscanthus, cord grass, and reed canary grass; fiber process residues such as corn fiber, beet pulp, pulp mill fines and rejects and sugar cane bagasse; sugar cane straw and sorghum; forestry wastes such as yellow poplar, aspen wood, other hardwoods, softwood and sawdust; and post-consumer waste paper products; as well as other crops or sufficiently abundant lignocellulosic material.

In another embodiment, biomass that is useful for the invention includes biomass that has a relatively high carbohydrate content, is relatively dense, and/or is relatively easy to collect, transport, store and/or handle.

In another embodiment of the invention, biomass that is useful includes corn cobs, corn stover, sugar cane bagasse, sugar cane straw, yellow poplar and switchgrass.

The lignocellulosic biomass may be derived from a single source, or biomass can comprise a mixture derived from more than one source; for example, biomass could comprise a mixture of corn cobs and corn stover, or a mixture of stems or stalks and leaves.

In the present method, the biomass dry weight is at an initial concentration of at least about 9% up to about 80% of the weight of the biomass-solvent suspension during pretreatment. More suitably, the dry weight of biomass is at a concentration of from about 15% to about 70%, 15% to about 60%, or about 15% to about 50% of the weight of the biomass-solvent suspension. The percent of biomass in the biomass-solvent suspension is kept high to reduce the total volume of pretreatment material, decreasing the amount of solvent and reagents required and making the process more economical.

The biomass may be used directly as obtained from the source, or may be subjected to some preprocessing, for example, energy may be applied to the biomass to reduce the size, increase the exposed surface area, and/or increase the accessibility of lignin and of cellulose, hemicellulose, and/or oligosaccharides present in the biomass to organosolv pretreatment and to saccharification enzymes used in the second step of the method. Energy means useful for reducing the size, increasing the exposed surface area, and/or increasing the accessibility of the lignin, and the cellulose, hemicellulose, and/or oligosaccharides present in the biomass to the organosolv pretreatment and to saccharification enzymes include, but are not limited to, milling, crushing, grinding, shredding, chopping, disc refining, ultrasound, and microwave. This application of energy may occur before or during pretreatment, before or during saccharification, or any combination thereof.

Drying prior to pretreatment may occur as well by conventional means, such as exposure at ambient temperature to vacuum or flowing air at atmospheric pressure and or heating in an oven at atmospheric pressure or a vacuum oven.

Pretreatment Conditions

Pretreatment of biomass with the solvent solution comprising organo-mercaptan, under alkaline conditions, is carried out in any suitable vessel. Typically the vessel is one that can withstand pressure, has a mechanism for heating, and has a mechanism for mixing the contents. Commercially available vessels include, for example, the Zipperclave® reactor (Autoclave Engineers, Erie, Pa.), the Jaygo reactor (Jaygo Manufacturing, Inc., Mahwah, N.J.), and a steam gun reactor (described in General Methods Autoclave Engineers, Erie, Pa.). Much larger scale reactors with similar capabilities may be used. Alternatively, the biomass and organosolv solution may be combined in one vessel, then transferred to another reactor. Also biomass may be pretreated in one vessel, then further processed in another reactor such as a steam gun reactor (described in General Methods; Autoclave Engineers, Erie, Pa.).

The pretreatment reaction may be performed in any suitable vessel, such as a batch reactor or a continuous reactor. One skilled in the art will recognize that at higher temperatures (above 100° C.), a pressure vessel is required. The suitable vessel may be equipped with a means, such as impellers, for agitating the biomass-organosolv mixture. Reactor design is discussed in Lin, K.-H., and Van Ness, H. C. (in Perry, R. H. and Chilton, C. H. (eds), Chemical Engineer's Handbook, $5^{th}$ Edition (1973) Chapter 4, McGraw-Hill, NY). The pretreatment reaction may be carried out either as a batch, or a continuous process.

Prior to contacting the biomass with solvent, vacuum may be applied to the vessel containing the biomass. By evacuating air from the pores of the biomass, better penetration of the solvent into the biomass may be achieved. The time period for applying vacuum and the amount of negative pressure that is applied to the biomass will depend on the type of biomass and can be determined empirically so as to achieve optimal pretreatment of the biomass (as measured by the production of fermentable sugars following saccharification).

The heating of the biomass with solvent is carried out at a temperature of from about 100° C. to about 220° C., about 150° C. to 200° C., or about 165° C. to about 195° C. The heated solution may be cooled rapidly to room temperature. In still another embodiment, the heating of the biomass is carried out at a temperature of about 180° C. Heating of the biomass-solvent suspension may occur for about 5 minutes to about 5 hours, or for about 30 minutes to about 3 hours, or more preferably from about 1 to 2 hours.

One condition that is significant to optimal pretreatment is the pH relative to the pKa of the thiol group of the organo-mercaptan. This molecule is a superior nucleophile and reductant for lignin fragmentation under conditions where the thiol group is deprotonated to form the thiolate. Reactions that thiolates can participate in that lead to lignin fragmentation are: a) substitution of the aryl ethers and b) reduction of quinone methides resulting in release of a phenoxyl radical derived from the β-aryl ether.

For thioglycolic acid, the pKa in water is 10.31, the pH at which the thiol concentration equals that of the thiolate. Particularly suitable for this invention is a pH of the biomass-EtOH in $H_2O$ and organo-mercaptan mixture that is greater than or equal to the organo-mercaptan pKa but less than pH 14. More specifically, the pH could be between the pKa+1 and pH 14. Even more specifically, the pH in the range of from about pKa+2 and pH 14 could be most useful for the present invention. Further, the pH may be adjusted using one or more base that can also act as a nucleophile that further serves to fragment the lignin and promote its extraction and that further protects the polysaccharide against "peeling" at alkaline pH. Such nucleophiles include ammonia, and more particularly alkylamines.

The pretreatment of biomass with the solvent solution and one or more alkylamine occurs under alkaline conditions at a pH that is equal to or greater than the pKa of the nucleophiles present. Deprotonation typically increases the reactivity of the nucleophile. The nucleophiles present, in addition to alkylamine, can include ammonia, thiols, polysulfides, or hydrosulfide.

For the pretreatment methods described herein, the temperature, pH, time of pretreatment and concentration of reactants such as the organic solvent and alkylamine solutions and the concentration of one or more additional reagents, biomass concentration, biomass type and biomass particle size are related; thus these variables may be adjusted as necessary for each type of biomass to optimize the pretreatment processes described herein.

Following pretreatment at elevated temperature, the biomass is filtered under pressure. The filtration may either be preceded or not by cooling. Following filtration, the biomass may be washed one or more times with hydrated organic solvent at elevated or at ambient temperature. It may then either be washed with water or dried to remove the organic solvent and then saccharified. Methods for drying the biomass were described above.

To assess performance of the pretreatment, i.e., the production of readily saccharifiable carbohydrate-enriched biomass and subsequent saccharification, separately or together, the theoretical yield of sugars derivable from the starting biomass can be determined and compared to measured yields. Pretreatment performance may be further assessed by relating how enzyme loadings affect target product yields in overall system performance.

Further Processing
Saccharification

Following pretreatment, the readily saccharifiable carbohydrate-enriched biomass comprises a mixture of organic solvent, one or more organo-mercaptan and any additional components of the solvent solution such as alkylamines or ammonia; fragmented and extracted lignin; and polysaccharides. Prior to further processing, the one or more organo-mercaptans and/or additional solvent components such as alkylamines or ammonia and lignin fragments may be removed from the pretreated biomass by filtration and washing the sample with EtOH in $H_2O$ (0% to 100% EtOH v/v) or water. The biomass may then either be washed with water to remove EtOH or be dried resulting in carbohydrate-enriched, readily saccharifiable biomass and the concentration of glucan, xylan and acid-insoluble lignin content of said biomass may be determined using analytical means well known in the art. It is a real benefit of this invention that the pretreated biomass can be either washed with water or dried for saccharification. The readily saccharifiable biomass may then be further hydrolyzed in the presence of a saccharification enzyme consortium to release oligosaccharides and/or monosaccharides in a hydrolysate.

Surfactants such as Tween 20 or Tween 80 or polyoxyethylenes such as PEG 2000, 4000 or 8000 may be added to improve the saccharification process (U.S. Pat. No. 7,354,743 B2, incorporated herein by reference). The addition of surfactant (e.g., Tween 20) to the enzymatic saccharification often enhances the rate and yield of monomeric sugar release. It is likely that the surfactant coats any residual lignin, decreasing the non-productive binding of the enzyme to the lignin. An alternative approach is to either enhance the extraction of lignin in the pretreatment or to modify the lignin chemically such that less enzyme is lost to lignin adsorption.

Saccharification enzymes and methods for biomass treatment are reviewed in Lynd, L. R., et al., (Microbiol. Mol. Biol. Rev., 66:506-577, 2002). The saccharification enzyme consortium may comprise one or more glycosidases; the glycosidases may be selected from the group consisting of cellulose-hydrolyzing glycosidases, hemicellulose-hydrolyzing glycosidases, and starch-hydrolyzing glycosidases. Other enzymes in the saccharification enzyme consortium may include peptidases, lipases, ligninases and esterases.

The saccharification enzyme consortium comprises one or more enzymes selected primarily, but not exclusively, from the group "glycosidases" which hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem., 223: 1-5, 1994; Eur. J. Biochem., 232:1-6, 1995; Eur. J. Biochem., 237:1-5, 1996; Eur. J. Biochem., 250:1-6, 1997; and Eur. J. Biochem., 264:610-650 1999, respectively]) of the general group "hydrolases" (EC 3.). Glycosidases useful in the present method can be categorized by the biomass component that they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabino-xylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the biomass. It is well known in the art that microorganisms that produce polysaccharide-hydrolyzing enzymes often exhibit an activity, such as cellulose degradation, that is catalyzed by several enzymes or a group of enzymes having different substrate specificities. Thus, a "cellulase" from a microorganism may comprise a group of enzymes, all of which may contribute to the cellulose-degrading activity. Commercial or non-commercial enzyme preparations, such as cellulase, may comprise numerous enzymes depending on the purification scheme utilized to obtain the enzyme. Thus, the saccharification enzyme consortium of the present method may comprise enzyme activity, such as "cellulase", however it is recognized that this activity may be catalyzed by more than one enzyme.

Saccharification enzymes may be obtained commercially, in isolated form, such as Spezyme® CP cellulase (Genencor International, Rochester, N.Y.) and Multifect® xylanase (Genencor). In addition, saccharification enzymes may be expressed in host microorganisms at the biofuels plant, including using recombinant microorganisms.

One skilled in the art would know how to determine the effective amount of enzymes to use in the consortium and adjust conditions for optimal enzyme activity. One skilled in the art would also know how to optimize the classes of enzyme activities required within the consortium to obtain optimal saccharification of a given pretreatment product under the selected conditions.

Preferably the saccharification reaction is performed at or near the temperature and pH optima for the saccharification enzymes. The temperature optimum used with the saccharification enzyme consortium in the present method ranges from about 15° C. to about 100° C. In another embodiment, the temperature optimum ranges from about 20° C. to about 80° C. and most typically 45-50° C. The pH optimum can range from about 2 to about 11. In another embodiment, the pH optimum used with the saccharification enzyme consortium in the present method ranges from about 4 to about 5.5.

The saccharification can be performed for a time of about several min to about 120 hours, and preferably from about several minutes to about 48 hours. The time for the reaction will depend on enzyme concentration and specific activity, as well as the substrate used, its concentration (i.e., solids loading) and the environmental conditions, such as temperature and pH. One skilled in the art can readily determine optimal conditions of temperature, pH and time to be used with a particular substrate and saccharification enzyme(s) consortium.

The saccharification can be performed batch-wise or as a continuous process. The saccharification can also be performed in one step, or in a number of steps. For example, different enzymes required for saccharification may exhibit different pH or temperature optima. A primary treatment can be performed with enzyme(s) at one temperature and pH, followed by secondary or tertiary (or more) treatments with different enzyme(s) at different temperatures and/or pH. In addition, treatment with different enzymes in sequential steps may be at the same pH and/or temperature, or different pHs and temperatures, such as using cellulases stable and more active at higher pHs and temperatures followed by hemicellulases that are active at lower pHs and temperatures.

The degree of solubilization of sugars from biomass following saccharification can be monitored by measuring the release of monosaccharides and oligosaccharides. Methods to measure monosaccharides and oligosaccharides are well known in the art. For example, the concentration of reducing sugars can be determined using the 1,3-dinitrosalicylic (DNS) acid assay (Miller, G. L., Anal. Chem., 31: 426-428, 1959). Alternatively, sugars can Be Measured By HPLC Using An Appropriate Column As Described Below.

Fermentation to Target Products

The readily saccharifiable biomass produced by the present methods may be hydrolyzed by enzymes as described above to produce fermentable sugars which then can be fermented into a target product. "Fermentation" refers to any fermentation process or any process comprising a fermentation step. Target products include, without limitation alcohols (e.g., arabinitol, butanol, ethanol, glycerol, methanol, 1,3-propanediol, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); ketones (e.g., acetone); amino acids (e.g., aspartic acid, glutamic acid, glycine, lysine, serine, and threonine); gases (e.g., methane, hydrogen ($H_2$), carbon dioxide ($CO_2$), and carbon monoxide (CO)).

Fermentation processes also include processes used in the consumable alcohol industry (e.g., beer and wine), dairy industry (e.g., fermented dairy products), leather industry, and tobacco industry.

Further to the above, the sugars produced from saccharifying the pretreated biomass as described herein may be used to produce in general, organic products, chemicals, fuels, commodity and specialty chemicals such as xylose, acetone, acetate, glycine, lysine, organic acids (e.g., lactic acid), 1,3-propanediol, butanediol, glycerol, ethylene glycol, furfural, polyhydroxy-alkanoates, cis,cis-muconic acid, and animal feed (Lynd, L. R., Wyman, C. E., and Gerngross, T. U., Biocom. Eng. Biotechnol. Prog., 15: 777-793, 1999; and Philippidis, G. P., Cellulose bioconversion technology, in Handbook on Bioethanol: Production and Utilization, Wyman, C. E., ed., Taylor & Francis, Washington, D.C., 179-212, 1996; and Ryu, D. D. Y., and Mandels, M., Cellulases: biosynthesis and applications, Enz. Microb. Technol., 2: 91-102, 1980).

Potential coproduction of products may also be produced, such as multiple organic products from fermentable carbohydrate. Lignin-rich residues remaining after pretreatment and fermentation can be converted to lignin-derived chemicals, chemical building blocks or used for power production.

Conventional methods of fermentation and/or saccharification are known in the art including, but not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC).

SHF uses separate process steps to first enzymatically hydrolyze cellulose to sugars such as glucose and xylose and then ferment the sugars to ethanol. In SSF, the enzymatic hydrolysis of cellulose and the fermentation of glucose to ethanol is combined in one step (Philippidis, G. P., supra). SSCF includes the cofermentation of multiple sugars (Sheehan, J., and Himmel, M., Biotechnol. Prog. 15: 817-827, 1999). HHF includes two separate steps carried out in the same reactor but at different temperatures, i.e., high temperature enzymatic saccharification followed by SSF at a lower temperature that the fermentation strain can tolerate. DMC combines all three processes (cellulase production, cellulose hydrolysis, and fermentation) in one step (Lynd, L. R., Weimer, P. J., van Zyl, W. H., and Pretorius, I. S., Microbiol. Mol. Biol. Rev., 66: 506-577, 2002).

These processes may be used to produce target products from the readily saccharifiable biomass produced by the pretreatment methods described herein.

Advantages Of The Present Methods

Thiol reagents, such as organo-mercaptans, are among the best soft nucleophiles. By incorporating organo-mercaptans into the organic solvent process under alkaline conditions (due to the presence of alkali metal or alkaline earth hydroxide or ammonia or alkylamine or a combination thereof), the anionic thiolate, is primed to carry out substitution reactions on the aryl ethers of the lignin. The alkaline conditions also favor the formation of quinone methides from lignin. These are also readily attacked by thiols. The presence of ammonia and/or alkylamines, in addition to raising the pH, supplements the thiol nucleophilic chemistry in attacking the lignin as well as protecting the polysaccharide against "peeling" reactions, that result in monosaccharide release and loss at high pH. The use of alkylamines and/or ammonia as bases avoids the generation of an inorganic waste stream which would otherwise add to the financial and environmental cost of the process. The organo-mercaptans can also act as reducing agents, promoting the reduction of quinone methides, eliminating β-aryl ethers as phenoxyl radicals and protecting sugar residues from oxidative reactions. The use of organo-mercaptans in the lignocellulosic biomass pretreatment process therefore enhances the fragmentation of lignin and increases the selectivity of lignin extraction with respect to carbohydrate, producing carbohydrate-enriched biomass that is highly susceptible to enzymatic saccharification. It is also possible that thioglycolate, in substitution reactions that displace lignin aryl ethers, introduces carboxyl groups into lignin fragments, thereby increasing their hydrophilicity, making them more soluble in aqueous medium and less likely to adsorb cellulolytic enzyme.

Methods described in this invention for pretreatment of the lignocellulosic biomass using organic solvent-mediated fragmentation and selective extraction of lignin at elevated temperatures under alkaline conditions in combination with organo-mercaptans and various nucleophiles provide a cost-effective process to obtain carbohydrate-enriched biomass for enzymatic saccharification. Such biomass then, produces very high yields of fermentable sugars (glucose, as well as xylose) for their bioconversion to value-added chemicals and fuels.

EXAMPLES

Pretreatment of Biomass to Obtain Readily Saccharifiable Biomass

The goal of the experimental work described below was to develop an economical pretreatment process for lignocellulose that maximized lignin extraction and minimized sugar loss in the pretreatment, producing a readily saccharifiable carbohydrate-enriched biomass that upon enzymatic saccharification, would give maximal monomeric sugar yields. The approach adopted was to selectively fragment and extract the lignin into a suitable solvent while retaining the sugars in the solids residue. The following experiments show that using an organic solvent mixture, selective extraction medium for lignin was developed that combined the presence of one or more organo-mercaptan and nucleophiles like alkylamines and $NH_3$ for selective extraction of lignin. It was found that the combined presence of an organic solvent and organo-mercaptan and alkylamine and optionally certain nucleophiles like $NH_3$, selectively fragmented and dissolved the lignin components of biomass providing for the generation of readily saccharifiable carbohydrate-enriched biomass.

Ground sugar cane bagasse, which was milled in a Wiley Knife mill through a 1 mm sieve, was used in all Examples.

The following abbreviations are used in the Examples: "HPLC" is High Performance Liquid Chromatography, "C" is degrees Centigrade or Celsius; "%" is percent; "wt" is weight; "w/w" is weight for weight; "mL" is milliliter; "OD" is outer diameter; "ID" is internal diameter; "h" is hour(s); "rpm" is revolution per minute; "EtOH" is ethanol; "mg/g" is milligram per gram; "g/100 mL" is gram per 100 milliliters; "N" is normal; "g" is gram; "NaOH" is sodium hydroxide; "w/v" is weight per volume; "v/v" is volume for volume; "mm" is millimeter; "mL/min" is milliliter per minute; "min" is minutes; "mM" is millimolar.

Materials

Sulfuric acid, ammonium hydroxide, acetic acid, acetamide, yeast extract, 2-morpholinoethanesulfonic acid (MES), potassium phosphate, glucose, xylose, tryptone, sodium chloride, citric acid acid, monomethyl and dimethylamine were obtained from Sigma-Aldrich (St. Louis, Mo.). Spezyme CP and Multifect CX12L were from Genecor (Genencor International, Palo Alto, Calif.) and Novozyme 188 was from Novozyme (Bagsvaerd, Denmark).

Example 1

Effective Ethanol Concentration

The purpose of this Example was to examine the effect of the concentration of solvent (e.g., ethanol) in water on the recovery of carbohydrate and on the solubilization/extraction of lignin in the absence of pH control. Bagasse (0.2 g, 95.78% dry matter) was suspended in 1.56 mL of an EtOH in water solution containing various concentrations (from 0 to 80%) of EtOH. The suspensions were loaded into type 316 stainless steel tubing (¼ inches ID, ⅜ inches OD, 4 inches long) capped by Swagelock fittings (Penn Fluid System Technologies, Huntingdon Valley, Pa.). These were placed in a fluidized sand bath (Techne Model SBS-4, Techne Inc., Burlington, N.J.) and heated at 180° C. for 2 h and cooled rapidly by plunging into a water bath at room temperature. The samples were removed from the tubes and filtered by centrifugation at 14,000 rpm using Spin-X filters (Costar, Corning Inc., Corning N.Y. 14831) at room temperature in a table top centrifuge (Spectrifuge 16M, Labnet International Inc., Edison, N.J.) to remove the dissolved lignin. The retentate of each sample was washed (4×) with 0.5 mL of EtOH in $H_2O$ using the same EtOH concentration as used in the 180° C. treatment (0-80% EtOH in $H_2O$). The samples were then allowed to air dry at room temperature (to ~92% dry matter) and the glucan, xylan and acid-insoluble lignin contents of the residues determined using the National Renewable Energy Laboratory (NREL) procedure (Determination of Structural Carbohydrates and Lignin in Biomass—Version 2006, Amie Sluiter et al., available from the NREL website.

Subsequent Enzymatic Saccharification

The air-dried sample prepared above was suspended in 50 mM citrate buffer, pH 4.6 at a ~14% solids loading. The saccharification enzymes, e.g. Spezyme CP, Multifect CX12L and Novozyme 188 were added at concentrations of 6:3:6 mg/g cellulose, respectively. Also added were 1% (w/v) Tween 20 and 0.01% (w/v) $NaN_3$, the latter to prevent microbial growth. Samples (~0.4 mL) were placed in screw cap vials containing two 5 mm glass beads and incubated at 46° C. on a rotary shaker run at 250 rpm. Aliquots were removed for analysis at 4 h and at every 24 h interval from the start and diluted 41.25-fold with 0.01 N $H_2SO_4$. The samples were then filtered through Spin-X filters and the filtrates were analyzed by HPLC (Agilent series 1100/1200, Agilent Technologies, Wilmington, Del.). A BioRad HPX-87H Aminex column (Bio-Rad Laboratories, Hercules Calif.) was used to fractionate the released sugars using 0.01N $H_2SO_4$ as the mobile phase at a flow rate of 0.6 mL/min. The column was maintained at 60° C. A differential refractive index detector was used to detect the eluted sugars and was maintained at 55° C. The retention times for glucose, xylose and arabinose were 9.05, 9.72 and 10.63 min, respectively). Table 1A outlines the percentages of glucan and xylan recovery and the percent change in acid insoluble (AI) lignin content after pretreatments at EtOH concentrations of 0%-80%.

TABLE 1A

Glucan and xylan recovery following pretreatment according to Example 1

| Pretreatment (% EtOH in water) | % Glucan recovery in residue | % Xylan recovery in residue | Al lignin content % change |
|---|---|---|---|
| 0 | 83.0% | 29.0% | +27.6% |
| 20 | 88.7% | 30.8% | +15.2% |
| 40 | 86.0% | 57.6% | −10% |
| 60 | 91.9% | 87.4% | −25.6% |
| 80 | 88.6% | 91.1% | −28.8% |

Results shown in Table 1A indicate that lignin extraction increased with increasing EtOH content presumably because the solubility of lignin increased with increasing EtOH concentration. However, the amount of lignin extracted remained modest even at high ethanol concentrations.

Hemicellulose hydrolysis and the solubility of xylose oligomers decreases with increasing EtOH, increasing the recovery of xylan and xylose oligomers in the residue. The amount of acetate liberated by the pretreatment also decreased with increasing EtOH content, consistent with decreasing auto hydrolysis of the biomass at increasing EtOH concentration.

Table 1B shows the glucose and xylose yields after 96 h of enzymatic saccharification following pretreatment at different EtOH concentrations. The saccharification of cellulose increased when the concentration of EtOH in pretreatment was increased from 0 to 20%, but then declined with higher pretreatment concentrations of EtOH. A likely decrease in partial hydrolysis of lignin and cellulose (increase in degree of polymerization, of cellulose which lowered the glucose yield on subsequent saccharification—Table 1B) was observed at concentrations of more than 20% EtOH.

TABLE 1B

Monomeric glucose and xylose yields following enzymatic saccharification for 96 h, pretreated as described in Example 1

| % EtOH in water (v/v) | Glucose monomer saccharification only (% theoretical yield) | Xylose monomer saccharification only (% theoretical yield) | Glucose monomer overall yield (% theoretical yield) | Xylose monomer overall yield (% theoretical yield) |
|---|---|---|---|---|
| 0 | 38.43 | 34.98 | 31.86 | 10.16 |
| 20 | 44.48 | 45.52 | 39.46 | 14.01 |
| 40 | 29.62 | 38.55 | 25.45 | 22.23 |
| 60 | 16.81 | 24.64 | 15.45 | 21.52 |
| 80 | 6.8 | 7.22 | 6.02 | 7.01 |

The monomeric sugar recoveries (Table 1B), particularly of xylose, were quite poor at the lower EtOH concentrations. At low EtOH concentration, the acidic conditions, produced at high temperatures by hydrolysis of the acetyl groups of the hemicellulose, hydrolyze the hemicellulose. The solubilized xylose and some glucose is lost in the filtration and washes that follow the pretreatment. At higher EtOH concentrations there is less partial hydrolysis of the cellulose, hemicellulose and lignin which lowers the saccharification yield. The behavior at the low and high ethanol concentrations together produce low overall yields of monomeric glucose and xylose.

Example 2

Effect of Alkaline Organic Solvent Solution Pretreatment on Lignin Extraction

The purpose of this Example was to examine the effect of raising the pH of the organic solvent solution pretreatment at different EtOH in $H_2O$ ratios on carbohydrate retention and lignin extraction and on monomeric sugar during subsequent enzymatic saccharification. Given that autohydrolysis lowers the pH, hydrolyzes xylan, and promotes the loss of xylose, the pH of the pretreatment was elevated by the addition of NaOH. The effect of higher pH on xylose recovery is demonstrated below. Sugar cane bagasse (0.25 g, 95.78% dry matter) was suspended in 1.75 mL of a solvent containing EtOH (20-80% in water) and 8% NaOH (w/w biomass) plus 1 mg anthraquinone (AQ, a catalyst for lignin fragmentation). The initial pH of this solution was ~13.7. The suspensions were loaded into type 316 stainless steel tubing as in Example 1, capped, treated at 168° C. for 140 min and cooled in room-temperature water. The samples were removed from the pressure vessels, filtered, washed, air-dried and analyzed all as described above in Example 1. The glucan, xylan, arabinan contents and change in lignin content following pretreatment are shown in Table 2A.

Subsequent enzymatic saccharification was carried out as described in Example 1 except that the Spezyme:Multifect: Novozymes 188 ratio was 12:6:1.2 mg/g dry solids in the presence of 1% Tween 20 (w/v). Table 2B shows the monomeric sugar yields after 96 h of enzymatic saccharification of biomass previously pretreated at the different EtOH concentrations.

TABLE 2A

Glucan, xylan and arabinan yields following pretreatment according to Example 2

| Pretreatment % EtOH in water | % Glucan recovery in residue | % Xylan recovery in residue | % Arabinan recovery in residue | Al lignin content % change |
|---|---|---|---|---|
| 20 | 77.5% | 74.6% | 51.3% | −48 |
| 45 | 84.0% | 85.1% | 68.0% | −64 |
| 60 | 83.6% | 85.5% | 76.0% | −63 |
| 70 | 81.3% | 84.2% | 75.8% | −65 |
| 80 | 80.0% | 84.2% | 86.6% | −50 |

TABLE 2B

Monomeric glucose and xylose yields following enzymatic saccharification
for 96 h, pretreated as described in Example 2

| % EtOH in H$_2$O | Glucose monomer saccharification only (% theoretical yield) | Xylan monomer saccharification only (% theoretical yield) | Glucose monomer overall yield (% theoretical yield) | Xylose monomer overall yield (% theoretical yield) |
| --- | --- | --- | --- | --- |
| 20 | 57.72 | 68.56 | 44.7 | 51.2 |
| 45 | 58.19 | 73.08 | 48.9 | 62.2 |
| 60 | 49.51 | 64.56 | 41.4 | 55.2 |
| 70 | 24.48 | 39.06 | 19.9 | 32.9 |
| 80 | 0.63 | 1.33 | 0.5 | 1.1 |

As can be seen in Tables 2A and 2B, the alkaline conditions of this experiment substantially increased the retention of xylan in the pretreatment compared to the autohydrolysis experiments of Example 1. This effect was most pronounced at low EtOH concentrations. The NaOH prevented the solution from becoming acidic (final pH ~10.7) and therefore protected the hemicellulose from acid-catalyzed hydrolysis. In addition, significantly more lignin was extracted, presumably through base catalyzed fractionation of the lignin. The overall monomeric sugar yields following saccharification were substantially higher than those observed in Example 1. The higher sugar recovery and the greater lignin extraction in the pretreatment, increased the yields of the subsequent enzymatic saccharification. The xylose and glucose saccharification yields peaked at ~45% EtOH as a consequence of two opposing processes, i.e., the increasing extraction of lignin at higher EtOH which tends to increase the sugar yields, and the decreasing partial hydrolysis of hemicellulose and of lignin as the EtOH concentration is further increased. It is likely that the formation of quinone methides, which could repolymerize or react with sugars, and "peeling" and alkaline scission reactions of polysaccharide all together contribute to limit the overall sugar yields.

Example 3

Effective Pretreatment with Organ-Mercaptans

The purpose of this Example was to study the effect of organo-mercaptans (e.g., thioglycolate) in the solvent solution. Further, surfactants like Tween 20 often enhance the rate and yield of monomeric sugar release, but at an added cost. It is likely that the surfactant coats any residual lignin, decreasing the non-productive binding of the enzyme to the lignin. A cost-savings could be realized by an improved pretreatment that obviates the need for surfactant in the saccharification step. Such an improvement could be accomplished by further enhancing the extraction of lignin in the pretreatment or by modifying the residual lignin chemically such that less enzyme is lost to lignin adsorption during saccharification.

In this Example, pretreatment was performed as in Example 1 except that sugar cane bagasse (0.375 g, 95.78% dry matter) was suspended in 1.125 mL of solvent containing 70% EtOH in H$_2$O (v/v) containing 14% MA with and without 2% thioglycolic acid, 2% glycolic acid or 2% glycine (all w/w biomass). The suspensions were loaded into type 316 stainless steel pressure vessels (3/16 inches ID, 1/4 inches OD, 4 inches long), capped and treated as described above in Example 1, except that solids loading was higher. In addition, the pretreatment was performed at 187° C. for 1 h instead of at 180° C. for 2 h.

Figure 1B:
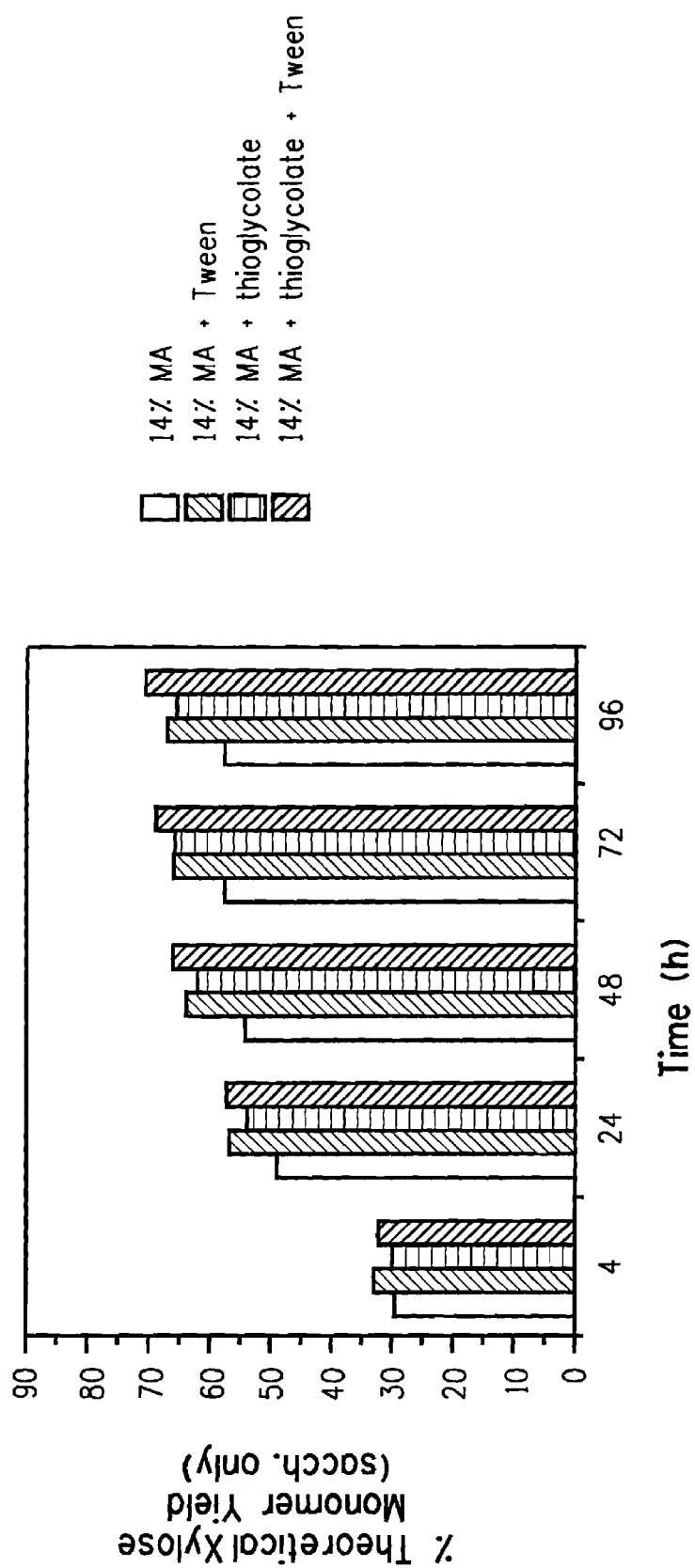

The subsequent enzymatic saccharification was performed for 96 h as described in Example 1 except that the Spezyme: Multifect:Novozymes 188 ratio was 6.68:3.34:1.67 mg/g dry solids in the presence and absence of 1% Tween 20 (w/v) at a solids loading of 14% (w/w). FIG. 1A shows the release of monomeric glucose upon enzymatic saccharification in the presence and absence of Tween following pretreatment at 187° C. for 1 h in 70% EtOH/H$_2$O and 14% MA with or without 2% thioglycolate. FIG. 1B shows the release of monomeric xylose upon enzymatic saccharification in the presence and absence of Tween following similar pretreatment in the presence and absence of thioglycolate. The addition of 2% thioglycolic acid (w/w biomass) to 70% EtOH/H$_2$O (v/v) plus 14% MA (w/w biomass) in the pretreatment significantly stimulated the enzymatic saccharification rate and yield of monomeric sugar in the absence of Tween 20. The comparison of the saccharification kinetics in the presence and absence of 1% Tween 20 and with and without 2% thioglycolic acid in the pretreatment (FIGS. 1A and 1B) shows that thioglycolic acid stimulated the saccharification rate and yield to the point where Tween 20 had less influence on both.

In order to understand the nature of the thioglycolic acid chemistry, similar experiments were performed with glycolic acid and glycine in which the —SH of the thioglycolic acid are replaced with —OH and —NH, respectively.

Figure 2A:
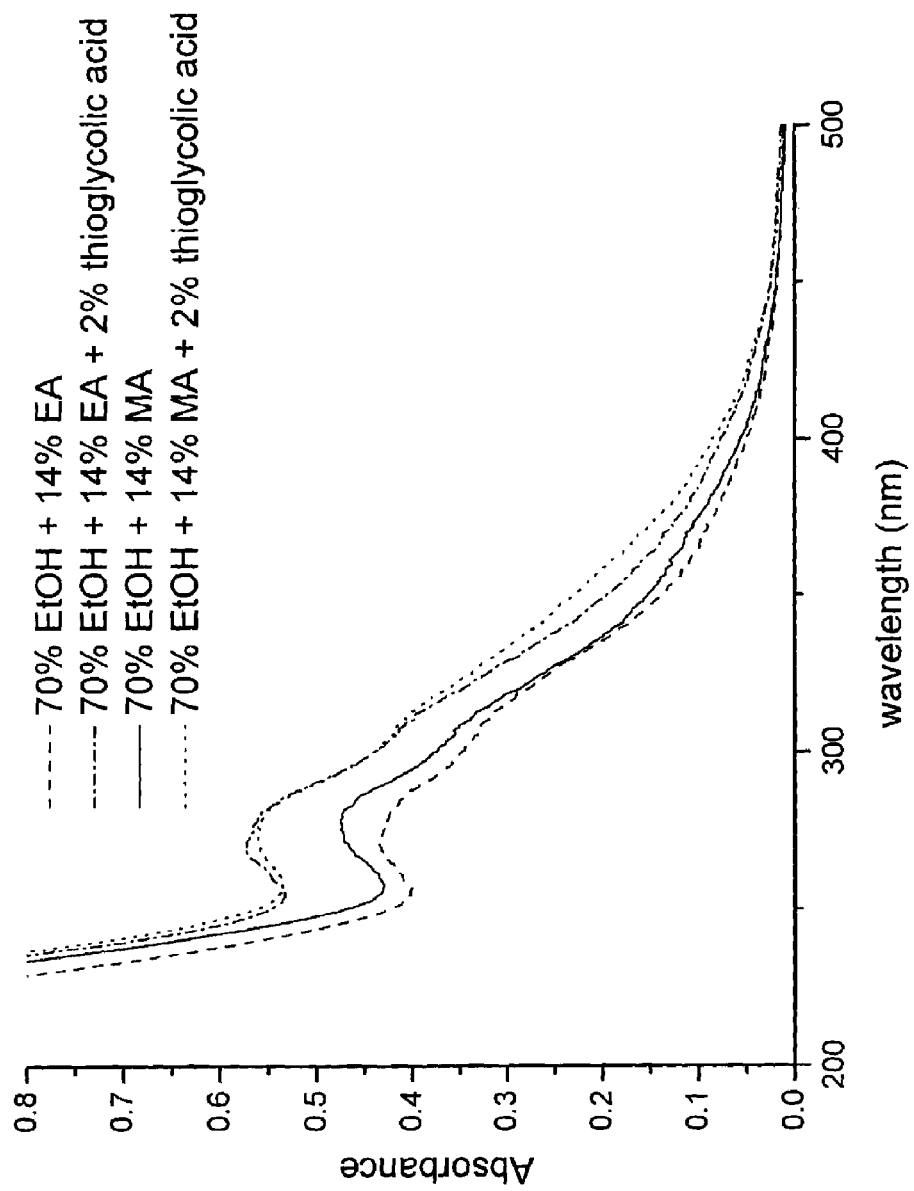
FIGS. 2A and 2B—FIG. 2A shows the UV absorbance spectra of filtrates (diluted 1:5000 with 70% EtOH in $H_2O$ (v/v)) following pretreatment at 187° C. for 1 hour in 70% EtOH in $H_2O$ (v/v) plus 14% methylamine (w/w biomass) and with 14% methylamine (w/w biomass) plus 2% thioglycolic acid (w/w biomass) and in 70% EtOH in $H_2O$ (v/v) plus 14% ethylamine (w/w biomass) and with 14% ethylamine (w/w biomass) plus 2% thioglycolic acid (w/w biomass).
Figure 2B:
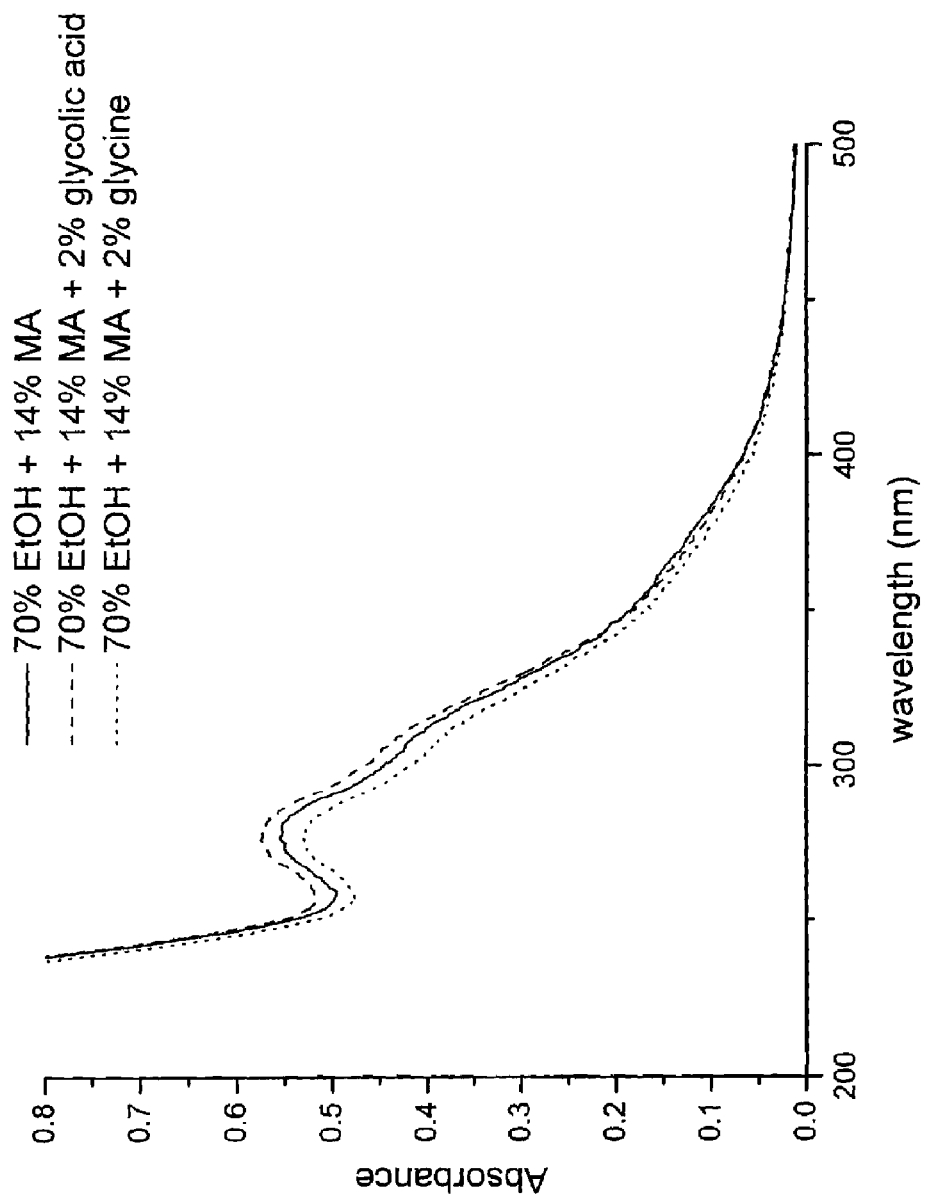

FIG. 2A shows the enhancement by thioglycolic acid of the extraction of lignin (greater UV absorption) in the pretreatment described above in the presence of methylamine. In contrast, there was little difference in the amplitude of the UV spectrum of the biomass treated with 70% EtOH/H$_2$O (v/v) plus 14% MA (w/w biomass) alone compared to 70% EtOH in H$_2$O (v/v) plus 14% MA plus 2% glycolic acid or 2% glycine (w/w biomass) (FIG. 2B).

As can be seen in Table 3, the comparison after 96 h of enzymatic saccharification in the absence of Tween 20 following pretreatment with 70% EtOH/H$_2$O (v/v) plus 14% MA (w/w biomass) containing either thioglycolic acid, glycolic acid or glycine indicated that the thioglycolic acid gave a significantly higher saccharification rate and yield than did either glycolic acid or glycine. It was concluded that the —SH group was responsible for the reactivity of the thioglycolic acid. The thioglycolic acid likely reacted with quinone methide intermediates produced in the fragmentation of the lignin under alkaline conditions either by reducing the quinone methide or by doing addition reactions to the quinone methides or by substituting for the α-and/or β-aryl ether components of lignin. These reactions likely promote further fragmentation and extraction of the lignin (FIG. 2). The glycolic acid and glycine were much less reactive or unreactive.

TABLE 3

Glucan and xylan yields following pretreatment and monomeric glucose and xylose yields following enzymatic saccharification with and without Tween 20 according to Example 3

| Sample 70% EtOH/H$_2$O (w/v) plus (w/w biomass) | % Glucan recovery in solids | % Xylan recovery in solids | Glucose monomer sacch. only (% theoretical yield) without Tween | Xylose monomer sacch. only (% theoretical yield) without Tween | Glucose monomer sacch. only (% theoretical yield) with Tween | Xylose monomer sacch. only (% theoretical yield) with Tween |
|---|---|---|---|---|---|---|
| 14% MA | 96.2 | 104.4 | 69.07 | 58.26 | 75.96 | 67.50 |
| 14% MA + 2% thioglycolic acid | 92.3% | 104.0% | 77.37 | 65.78 | 81.89 | 71.38 |
| 14% MA + 2% glycolic acid | 89.4% | 99.4% | 72.3 | 57.5 | 82.43 | 69.70 |
| 14% MA + 2% glycine | 97.0% | 103.7% | 73.06 | 59.85 | 77.63 | 68.27 |

Comparison of the HPLC profiles of oligomeric and monomeric sugar during enzymatic saccharification indicated that the addition of thioglycolic acid in the pretreatment (with no Tween in saccharification) produced a very similar profile to that observed after the addition of Tween 20 (with no thioglycolic acid in the pretreatment)—i.e., decreased xylobiose accompanied by increased monomeric xylose and increased cellobiose accompanied by increased monomeric glucose. The monomeric sugar yields for these two conditions were very similar (FIG. 1 and Table 3). These observations are consistent with increased lignin extraction produced by the addition of thioglycolic acid during the pretreatment (see Table 3). It is also possible that there is derivatization of the lignin by the thioglycolic acid to make the residual lignin more hydrophilic (addition of negative charge of carboxylate) resulting in a reduced loss of the cellulose and xylanase enzymes to non-productive binding. Such a decreased impact of lignin on saccharification is similar to what is thought to happen when Tween 20 is added to biomass pretreated in the absence of thioglycolate (i.e., Tween binds to lignin making it more hydrophilic). In summary, the inclusion of 2% thioglycolate (w/w biomass) in the pretreatment with 70% EtOH and alkylamine increased the lignin extraction and stimulated the saccharification yield of both glucose and xylose.

Example 4

Enhancement of Lignin Extraction by Adding Thioglycolate to Methylamine and Ethylamine During Pretreatment Pretreatment was performed as in Example 3 except that the 70%

EtOH in H$_2$O (v/v) solvent in which the bagasse was suspended contained 14% MA or 14% ethylamine (all w/w biomass) with and without 2% thioglycolic acid (w/w biomass). FIG. 2A shows the UV absorbance spectra of filtrates following pretreatment in 70% EtOH plus 14% alkylamine with or without 2% thioglycolate at 187° C. for 1 h. The increase in the UV absorption upon addition of thioglycolic acid to the pretreatment solvent in both cases, indicated that thioglycolic acid enhanced the fragmentation and extraction of lignin, consistent with the decrease of lignin present in the residue following pretreatment, filtration and wash with 70% EtOH in H$_2$O (v/v).

What is claimed is:

1. A method for producing carbohydrate-enriched biomass comprising
   (a) providing lignocellulosic biomass comprising lignin;
   (b) contacting the biomass of (a) with an organic solvent solution comprising water and one or more organo-mercaptan(s) under alkaline conditions whereby a biomass-solvent suspension is formed;
   (c) heating the biomass-solvent suspension to a temperature of about 100° C. to about 220° C. for about 5 minutes to about 5 hours whereby lignin is fragmented and is dissolved in the suspension; and
   (d) removing the dissolved lignin to produce a carbohydrate-enriched biomass.

2. The method of claim 1 whereby the dissolved lignin of step (d) is removed by filtration.

3. The method of claim 1 further comprising:
   (e) washing the biomass produced in step (d) with an organic solvent.

4. The method of claim 3, further comprising:
   (f) washing the biomass produced in step (e) with water to produce a readily saccharifiable carbohydrate-enriched biomass.

5. The method of claim 3 further comprising drying the biomass produced in step (e) to produce a readily saccharifiable carbohydrate-enriched biomass.

6. The method of claims 3 or 4, further comprising repeating steps (e) and (f) one or more times.

7. The method of claim 1 wherein the solvent solution further comprises a nucleophile selected from the group consisting of NH$_3$, one or more alkylamines, NaOH, sulfide reagents, and combinations thereof.

8. The method of claim 7 wherein the nucleophile is one or more alkylamine and said one or more alkylamine is at a concentration of up to 20% by weight of dry biomass.

9. The method of claim 1 wherein in step (b) the biomass dry weight is at an initial concentration of at least about 9% up to about 80% of the weight of the biomass-solvent suspension.

10. The method of claim 2, wherein the heated suspension of step (c) is cooled to room temperature before filtering in step (d).

11. The method of claim 2 further comprising evaporating off the solvent under vacuum of the filtered and washed biomass after step (e).

12. The method of claim 1 wherein the biomass is selected from the group consisting of switchgrass, waste paper, sludge from paper manufacture, corn fiber, corn cobs, corn husks, corn stover, grasses, wheat, wheat straw, hay, barley, barley straw, rice straw, sugar cane bagasse, sugar cane straw, yellow poplar, sorghum, soy, components obtained from processing of grains, trees, branches, roots, leaves, wood chips, sawdust, shrubs and bushes, vegetables, fruits, flowers, animal manure and combinations thereof.

13. A method of simultaneous fragmentation and selective extraction of lignin from lignocellulosic biomass to produce a substantially lignin-free biomass, the method comprising the steps of:
 (a) providing:
  1) an amount of lignocellulosic biomass;
  2) a multi-component solvent solution comprising from about 40% to about 70% ethanol in water;
  3) one or more organo-mercaptan(s); and
  4) and one or more alkylamine(s) under alkaline conditions;
 (b) contacting said biomass with the multi-component solvent solution of (a) to form a solvent-biomass mixture;
 (c) placing the solvent-biomass mixture in a sealed pressure vessel whereby the mixture of (b) is heated at a temperature of about 100° C. to about 220° C. for about 5 minutes to about 5 hours whereby lignin is fragmented and dissolved in the solvent;
 (d) removing the dissolved lignin of (c) by filtration; and
 (e) washing the residual biomass with organic solvent, whereby substantially lignin-free biomass is produced.

14. The method of claim 13 wherein the substantially lignin-free biomass is from about 60% to about 100% original weight of the biomass.

15. The method of claims 1 or 13 wherein said organic solvent solution further comprises one or additional component selected from the group consisting of alkali or alkaline earth hydroxides or carbonates, ammonia, thiols, polysulfides, hydrosulfide, and combinations thereof.

16. The method of claims 1 or 13 wherein the solvent solution, and any unreacted organo-mercaptan or other unreacted components are recyclable.

17. The method of claims 1 wherein said organic solvent solution comprises a solvent selected from the group consisting of alcohols, diols, and aprotic solvents.

18. The method of claim 17 wherein the organic solvent solution comprises a solvent selected from the group consisting of methanol, ethanol, propanol, butanol, pentanol and hexanol, isomers thereof, and diols thereof.

19. The method of claims 7 wherein the one or more alkylamines is selected from the group consisting of R—$NH_2$, $R_2$—NH, $R_3$N, ($H_2$N—R—$NH_2$), ($H_2$N—R($NH_2$)$_2$), (HO—R—$NH_2$), ((HO)$_2$—R—$NH_2$), (HO—R—($NH_2$)$_2$), (HS—R—$NH_2$), ((HS)$_2$—R—$NH_2$), (HS—R—($NH_2$)$_2$) and ($H_2$N—R(OH)(SH) and combinations thereof, wherein R is independently a monovalent, divalent or trivalent 1-6 carbon alkane, alkene or alkyne, linear, cyclic or branched.

20. The method of claim 19 wherein R is independently methyl, ethyl, propyl or butyl.

21. The method of claim 19 wherein the alkylamine is methylamine.

22. The method of claim 1 wherein the organo-mercaptan is selected from the group consisting of thioglycolate, 2-mercaptoethanol, dithiothreitol, dithioerythritol, cysteine and glutathione, methanethiol, mono-and disubstituted ethane, propane and butane thiols.

23. The method of claim 13 wherein the temperature of the step (c) is from about 165° C. to about 195° C.

* * * * *